US00PP20617P2

(12) United States Plant Patent
Pierce

(10) Patent No.: US PP20,617 P2
(45) Date of Patent: Dec. 29, 2009

(54) ***CALIBRACHOA* PLANT NAMED 'CAL MANG'**

(50) Latin Name: ***Calibrachoa* spp.**
Varietal Denomination: Cal Mang

(75) Inventor: Robert O. Pierce, Watsonville, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,431

(22) Filed: Nov. 10, 2008

(51) Int. Cl.
*A01H 5/00* (2006.01)

(52) U.S. Cl. ..... Plt./413

(58) Field of Classification Search ..... Plt./263, Plt./413
See application file for complete search history.

(56) References Cited

U.S. PATENT DOCUMENTS

PP19,865 P2 * 3/2009 Pierce ..... Plt./413

* cited by examiner

*Primary Examiner*—Susan B McCormick Ewoldt
(74) *Attorney, Agent, or Firm*—S. Matthew Edwards

(57) ABSTRACT

A new *Calibrachoa* plant named 'Cal Mang,' particularly distinguished by peachy-red toned flowers, is very floriferous, has a strong root system, a full habit that is free branching, and is bred for early flowering under shorter day lengths.

1 Drawing Sheet

Latin name of the genus and species of the plant claimed: *Calibrachoa* spp.

Varietal denomination: 'Cal Mang'.

BACKGROUND OF THE NEW PLANT

The present invention comprises a new *Calibrachoa,* botanically known as *Calibrachoa* spp. and hereinafter referred to by the variety name 'Cal Mang.'

'Cal Mang' is a product of a planned breeding program. The new cultivar 'Cal Mang' has peachy-red toned flowers, is very floriferous, has a strong root system, a full habit that is free branching, and is bred for early flowering under shorter day lengths.

'Cal Mang' originated from a hybridization in a controlled breeding program in Gilroy, Calif. U.S.A. The female parent was an patented hybrid seedling identified as 'Cal Goldey,' U.S. Plant Pat. No. 17,303, with gold color. 'Cal Goldey' has lighter green leaves, a more upright habit, and is later to flower than 'Cal Mang.'

The male parent of 'Cal Mang' was an unpatented hybrid seedling identified as '1295' with apricot color. '1295' has larger leaves, is later to flower, and less floriferous than 'Cal Mang.'

'Cal Mang' was selected as one flowering plant within the progeny of the stated cross in July 2005 in a controlled environment in Gilroy, Calif. U.S.A.

The first act of asexual reproduction of 'Cal Mang' was accomplished when vegetative cuttings taken from the initial selection in July 2005 in a controlled environment in Gilroy, Calif. U.S.A. The pollination took place in September 2004 and the seed sowing in April 2004 all in Gilroy, Calif., U.S.A.

Horticultural examination of plants grown from cuttings of the plant initiated in July 2005 in Gilroy, Calif. U.S.A., and continuing thereafter, has demonstrated that the combination of characteristics as herein disclosed for 'Cal Mang' are firmly fixed and are retained through successive generations of asexual reproduction.

'Cal Mang' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cal Mang' has not been made publicly available more than one year prior to the filing of this application.

DESCRIPTION OF THE DRAWINGS

The accompanying photographic drawing shows typical flower and foliage characteristics of 'Cal Mang' with colors being as true as possible with an illustration of this type. The photographic drawing shows three flowering potted plants of the new variety in a hanging basket and a close-up of the flowers. The hanging basket was grown and photographed in Hillscheid, Germany in the summer of 2006. The close-up plant was grown and photographed in Gilroy, Calif. U.S.A. in July 2008.

DETAILED BOTANICAL DESCRIPTION

The measurements were taken in April 2008, in Gilroy, Calif. U.S.A. on plants that were growing in one gallon pots. These plants were about 4–5 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. U.S.A. The following traits have been repeatedly observed and are determined to be basic characteristics of the new variety. The combination of these characteristics distinguishes this *Calibrachoa* as a new and distinct variety.

TABLE 1

DIFFERENCES BETWEEN THE NEW VARIETY 'CAL MANG' AND A SIMILAR VARIETY

| | 'Cal Mang' | 'Cal Peachy' |
|---|---|---|
| Flower color | Red-pink base color | Orange-red base color |
| Flower size | Larger | Smaller |
| Stem thickness | Thinner | Thicker |
| Leaf size | Larger leaves | Smaller leaves |

Plant:

*Form, growth and habit.*—Mounding and decumbent, well branched and a full plant.

*Plant height.*—10–13 cm.

*Plant height* (*inflorescence included*).—11–14 cm.

*Plant width.*—36–39 cm.

Foliage:

*Immature, leaf color, upper surface.*—RHS 146B.

*Lower surface.*—Closest to RHS 146A but less yellow.

*Mature, leaf color, upper surface.*—Closest to RHS 147A but lighter.

*Lower surface.*—Closest to RHS 146A but less yellow.

*Length.*—3.0–3.7 cm.

*Width.*—1.1–1.2 cm.

*Shape.*—Elliptical.

*Base shape.*—Acuminate.

*Apex shape.*—Obtuse.

*Margin.*—Serrate.

*Texture.*—Sparse glandular hairs.

*Color of veins, upper and lower surfaces.*—RHS 144A.

*Petiole color.*—RHS 144A.

*Petiole length.*—0.1–0.3 cm.

*Diameter of petiole.*—0.1 cm.

*Texture.*—Sparse glandular hairs.

Stem:

*Quantity of main branches.*—30–40.

*Quantity of secondary branches.*—4–6 per basal branch.

*Color of stem.*—Between RHS 144A and B.

*Length of stem.*—24–27 cm.

*Diameter.*—0.15–0.2 cm.

*Length of internodes.*—0.5–1.7 cm.

*Texture.*—Glandular hairs of various sizes.

*Color of pedicel.*—RHS 146C.

*Length of pedicel.*—2.5–3.7 cm.

*Diameter of pedicel.*—0.1 cm.

*Texture of pedicel.*—Glandular hairs of various sizes.

Inflorescence:

*Type.*—Flowers solitary in upper leaf axis; flowers face mainly horizontally, mostly 5-fused lobes forming a funnel form flower.

*Quantity of inflorescences per plant.*—Approximately 50.

*Lastingness of individual flowers.*—About 7–9 days.

*Fragrance.*—None.

*Duration of flowering.*—Continuous flowering throughout the Summer.

*Immature, color petals, upper surface.*—RHS 54A base color; RHS 46A; RHS 187B mid veins, RHS 179c veins.

*Color petals, lower surface.*—RHS 36C; RHS N199B mid veins.

*Mature, color petals, upper surface.*—RHS 55B base color, fading to RHS N155B; RHS 55B flush around the margins; RHS 46B, edged with RHS 37 A to B at the corolla opening; RHS 179B mid veins, RHS 179C veins.

*Color petals, lower surface.*—RHS 36C; RHS N199B mid veins.

*Flower horizontal diameter.*—3.7–4.1 cm.

*Flower height* (*vertical*).—3.6–4.3 cm.

*Apex shape.*—Slightly retuse.

*Margin.*—Entire.

*Waviness of petals.*—Slight.

*Petal lobation.*—Moderate.

*Petal texture.*—Papillose, but surfaces.

*Corolla tube color inside.*—RHS 7A; RHS 165D veins.

*Corolla tube color outside.*—RHS 7D; RHS 199C veins.

*Corolla tube length.*—1.5–2.0 cm.

Bud (just before opening):

*Color.*—RHS 160A; RHS 200B but a little more grey veins and petal margins.

*Length.*—1.0–2.3 cm.

*Width.*—0.3–0.5 cm.

*Shape.*—Oblong.

*Number of sepals.*—5.

*Color of sepals, outer surface.*—RHS 146B, slightly lighter basally.

*Color of sepals, inner surface.*—RHS 146A, slightly lighter basally.

*Length of sepals.*—1.5–1.7cm.

*Width of sepals.*—0.4 cm.

*Sepal shape.*—Oblanceolate.

*Apex shape.*—Obtuse.

*Margins.*—Entire.

*Texture.*—Glandular hairs of various sizes.

Reproductive organs:

*Pistil.*—1.

*Length.*—1.4 cm.

*Style color.*—RHS 1B.

*Style length.*—1.3 cm.

*Stigma color.*—RHS 144B.

*Number of stamens.*—5.

*Color of filaments.*–RHS 4C.

*Length filaments.*—1.1–1.4 cm.

*Color of pollen.*—RHS 13B.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Calibrachoa* plant named 'Cal Mang,' substantially as illustrated and described herein.

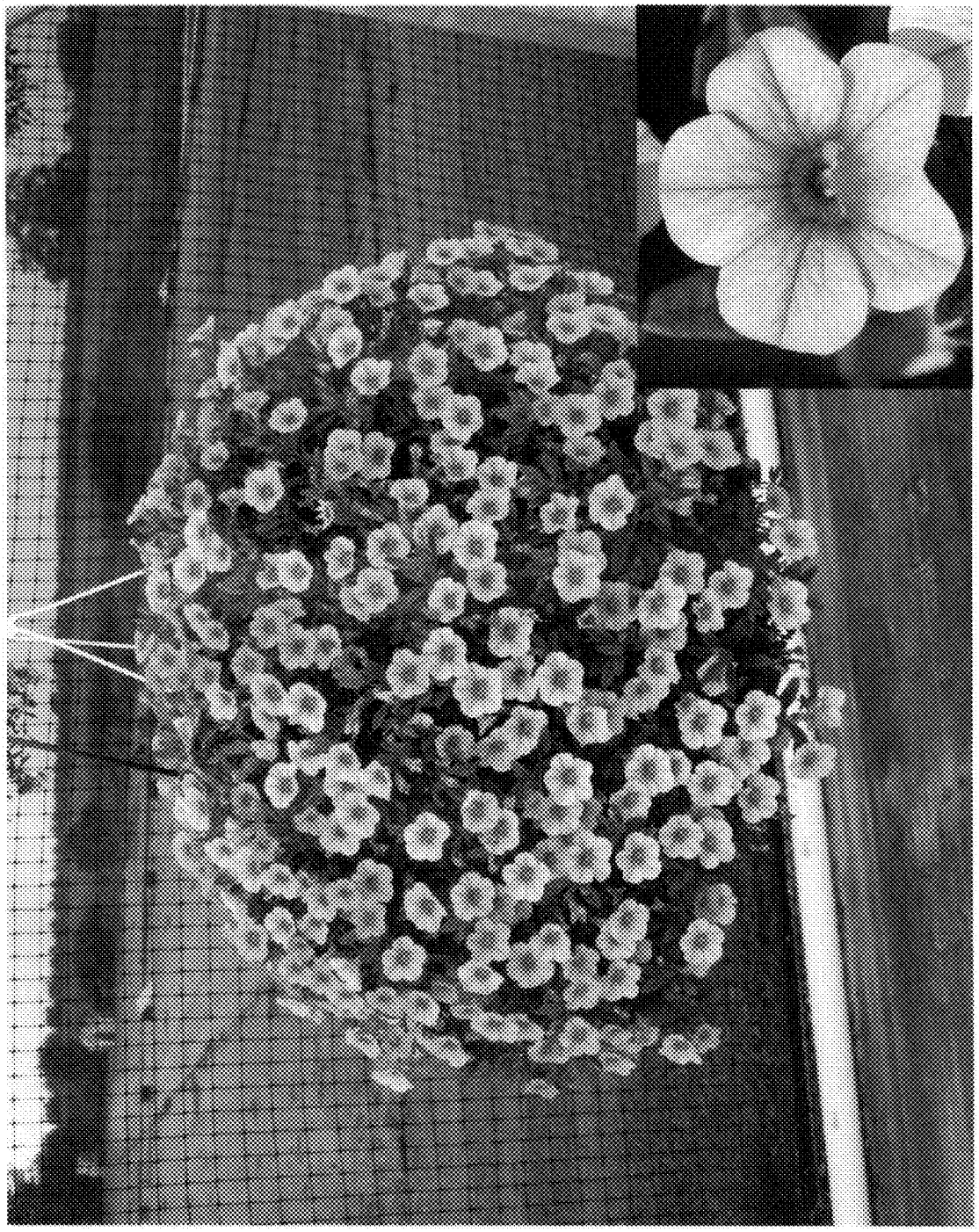

* * * * *